United States Patent [19]

Ehemann, Jr. et al.

[11] Patent Number: 5,640,019

[45] Date of Patent: Jun. 17, 1997

[54] METHOD OF DETERMINING THE QUALITY OF AN ALUMINIZED, LUMINESCENT SCREEN FOR A CRT

[75] Inventors: George Milton Ehemann, Jr., Lancaster; Richard LaPeruta, Jr., Lititz; Edward Richard Garrity, Jr., Lancaster, all of Pa.

[73] Assignee: Thomson Consumer Electronics, Inc., Indianapolis, Ind.

[21] Appl. No.: 554,311

[22] Filed: Nov. 8, 1995

[51] Int. Cl.$^6$ .................................................. G01N 21/64
[52] U.S. Cl. .................... 250/461.1; 250/459.1; 250/486.1
[58] Field of Search .................... 250/461.1, 459.1, 250/475.2, 486.1

[56] References Cited

U.S. PATENT DOCUMENTS

| | | |
|---|---|---|
| 3,679,968 | 7/1972 | Commercon et al. ............... 324/34 TK |
| 3,819,409 | 6/1974 | Phillips . |
| 3,858,081 | 12/1974 | Rehkopf et al. . |
| 3,878,457 | 4/1975 | Rogers .................... 324/34 TK |
| 4,584,481 | 4/1986 | Matey .................... 250/461.1 |
| 4,898,746 | 2/1990 | Opresko .................... 427/10 |
| 5,485,530 | 1/1996 | Lakowicz et al. .................... 250/459.1 |

*Primary Examiner*—Michael J. Tokar
*Assistant Examiner*—Virgil O. Tyler
*Attorney, Agent, or Firm*—Joseph S. Tripoli; Dennis H. Irlbeck; Vincent J. Coughlin, Jr.

[57] ABSTRACT

The invention relates to a method of determining the quality of an aluminized, luminescent screen 22 for a CRT 10. The luminescent screen 22 is disposed on an interior surface of a faceplate panel 12 with an aluminum layer 23 overlying the screen. The method includes the steps of: exposing the aluminum layer to ultraviolet radiation; and measuring the luminescence emitted by the screen through the aluminum layer.

5 Claims, 3 Drawing Sheets

METHOD OF DETERMINING THE QUALITY OF AN ALUMINIZED, LUMINESCENT SCREEN FOR A CRT

The present invention relates to a method of inspecting an aluminized faceplate panel for a cathode-ray tube (CRT) and, more particularly, to a method of determining the quality of an aluminum layer that overlies a luminescent screen before the faceplate panel is baked out and sealed to a funnel portion of the CRT.

BACKGROUND OF THE INVENTION

In the manufacturing of a luminescent screen for a CRT, three light emitting phosphors are deposited in triads across a useful screen area of an interior surface of a faceplate panel. Each triad is comprised of blue-, green- and red-emitting phosphor materials. It is known to provide an aluminum layer that overlies the phosphor materials to reflect light emitted by the phosphor materials outwardly through the viewing surface of the panel to the viewer. However, to maximize the light output, it is necessary to ensure that the aluminum layer is smooth and highly reflective. To accomplish this purpose, a layer of a filming material is disposed between the phosphor materials and the aluminum layer. The filming material provides a cushion that fills the interstitial spaces between the discrete phosphor particles and permits the aluminum layer to be applied as a smooth and uninterrupted surface. It is known in the art to test the integrity of the aluminized screen by measuring the thickness of the aluminum layer by means of an eddy current test. The eddy current method uses several pairs of inductor coils that are placed in proximity to the outside surface of the viewing faceplate of the panel, after aluminizing. One pair of coils is aimed at the center of the panel, and two other pairs are aimed at the 2 o'clock and 8 o'clock corners, respectively. One coil of each pair is excited by an rf power supply which induces a signal voltage in the second coil due to the very thin aluminum layer overlying the screen, on the inside surface of the panel. In the absence of aluminum, or in the case of very thin aluminum, the induced voltage signal is high, and the panel is rejected by comparing the voltage signal to a calibration standard. However, if the thickness of the aluminum layer is within the desired limits, the eddy current induced voltage in the second coil is lower and the aluminized screen is accepted. Unfortunately, the eddy current test is not foolproof and panels that have sufficient aluminum may be rejected because the aluminum layer is not smooth enough or continuous enough for eddy currents to form. Thus, a more reliable test that does not falsely reject good panels is desirable.

Subsequently, the faceplate panel is baked at a high temperature to remove the volatilizable constituents, including the layer of filming material. The aluminum layer contains small holes or pores through which the volatilizable constituents of the screen escape during screen bake without adversely affecting the reflectivity of the aluminum layer. The holes or pores in the aluminum layer can be utilized in a more reliable test which evaluates not only the quality of the aluminum layer, but also the effectiveness of the filming layer.

SUMMARY OF THE INVENTION

The invention relates to a method of determining the quality of an aluminized, luminescent screen for a CRT. The luminescent screen is disposed on an interior surface of a faceplate panel with an aluminum layer overlying the screen. The method includes the steps of: exposing the aluminum layer to ultraviolet radiation; and measuring the luminescence emitted by the screen through the aluminum layer.

BRIEF DESCRIPTION OF THE DRAWINGS

The invention will now be described in greater detail, with relation to the accompanying drawings, in which.

DETAILED DESCRIPTION OF THE PREFERRED EMBODIMENTS

Figure 1:
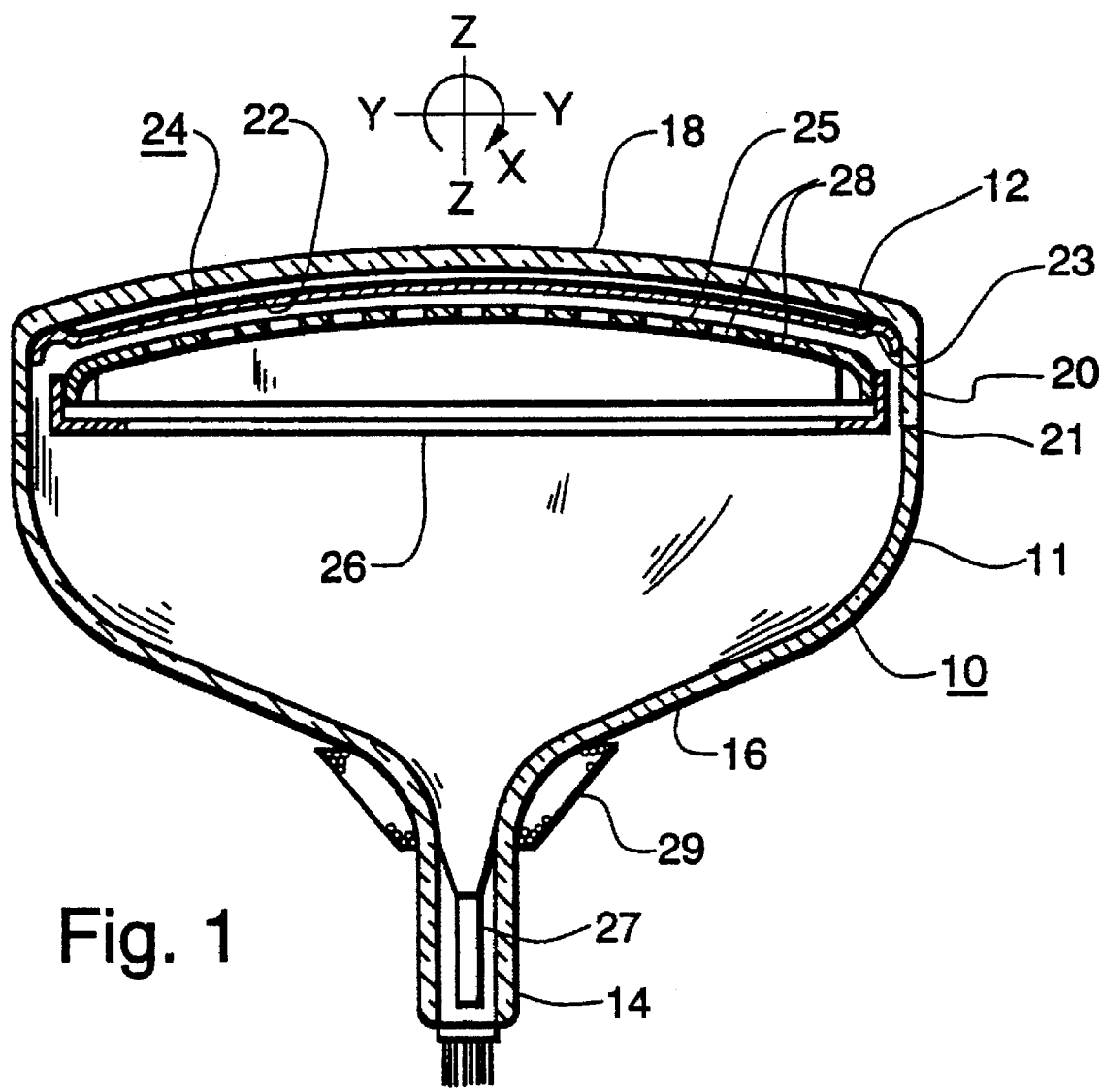
FIG. 1 is a partially cut away view of a CRT having a faceplate panel with an aluminized, luminescent screen.
Figure 3:
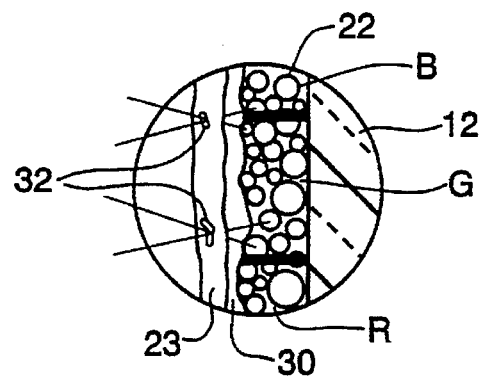
FIG. 3 shows a portion of the aluminized, luminescent screen within circle 3 of FIG. 2.

FIG. 1 shows a rectangular color CRT 10 having a glass envelope 11 comprising a rectangular faceplate panel 12 and a tubular neck 14 connected by a rectangular funnel 16. The panel 12 comprises a viewing faceplate 18 and a sidewall 20 which is sealed to the funnel 16 by a frit seal 21. The faceplate panel 12 includes two orthogonal axes: a major axis X-X, parallel to its wider dimension (usually horizontal), and a minor axis Y-Y, parallel to its narrower dimension (usually vertical). The major and minor axes are perpendicular to a central longitudinal axis Z-Z which extends through the center of the neck 14 and the center of the panel 12. A three-color luminescent phosphor screen 22 is provided on the interior surface of the panel 12. As shown in FIG. 3, the screen 22 is comprised of blue-, green- and red-emitting phosphor elements, B, G, R, respectively, which are arranged in cyclic groups, or triads, of the three emitting colors. The screen 22, preferably, is a line screen with t-he phosphor lines extending substantially parallel to the minor axis, Y-Y. Alternatively, the screen may be a dot screen. A thin layer of metal, such as aluminum, 23 overlies the luminescent phosphor screen 22 and in combination therewith forms a luminescent screen assembly 24. A multiapertured color selection electrode, such as a shadow mask, 25 is attached to a frame 26 and removably mounted, by conventional mean, not shown, in predetermined spaced relation to the luminescent screen assembly 24. An electron gun 27 is centrally mounted within the neck 14, to generate and direct three electron beams, also not shown, along convergent paths through openings 28 in the shadow mask 24, to the screen 22. The tube 10 is designed to be used with an external magnetic deflection yoke, such as yoke 29, located in the neighborhood of the funnel-to-neck junction. When activated, the yoke 29 subjects the three electron beams to magnetic fields which cause the beams to scan horizontally and vertically in a rectangular raster over the screen 22.

Figure 2:
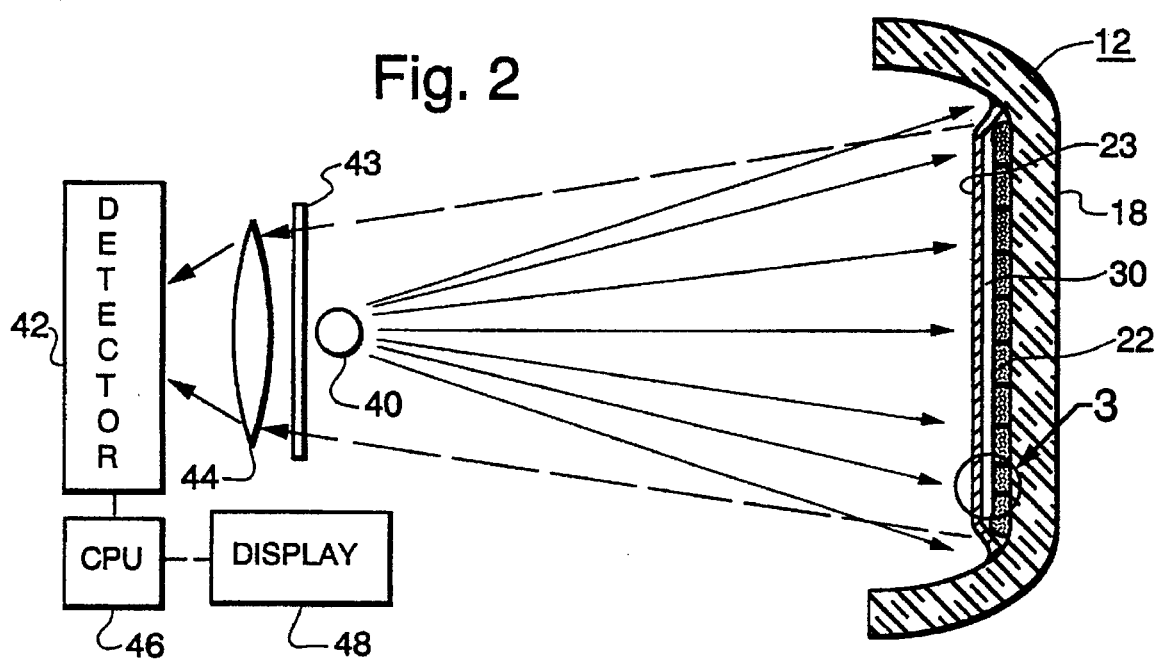
FIG. 2 is a schematic representation of a test setup according to the present invention.
Figure 4:
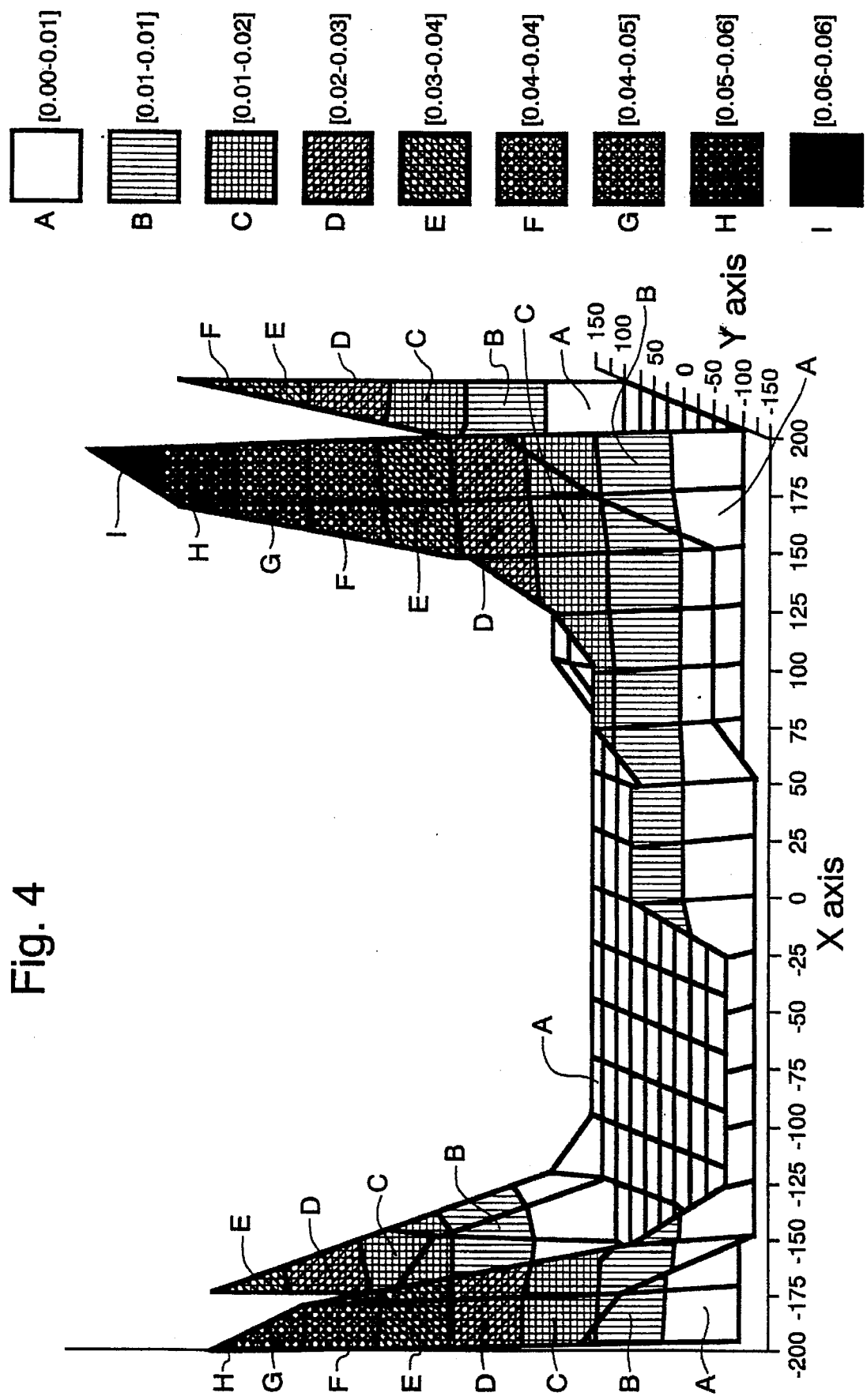
FIG. 4 shows a contour map of the luminescent screen using the test setup of FIG. 2.

In order to manufacture the luminescent screen assembly 24, a filming layer 30, shown in FIGS. 2 and 3, is provided between the luminescent screen 22 and the overlying aluminum layer 23. The filming layer 30 provides a smooth cushion over the relatively rough phosphor materials of the screen 22 on which the aluminum layer 23 is deposited. The filming layer 30 may be formed by spraying a solvent-based organic filming lacquer onto the phosphor materials of the screen 22, or by applying a water-based emulsion. The water-based emulsion is dispersed onto the rotating faceplate panel 12 as a limp stream, having a trajectory substantially tangential to the surface of the phosphor screen. The rotation of the faceplate panel spreads the water-based filming emulsion across the screen and towards the corners of the panel. The filming emulsion soaks into the voids between the individual phosphor particles as it spreads across the screen and bridges the voids therebetween, to provide the film layer 30 having the desired smooth surface. However, because the corners are the last areas of the screen to be coated with the filming emulsion, the voids between the individual phosphor particles in the corners of the screen are not as completely filled as they are in other areas of the screen and the film is not as smooth in the corners. Accordingly, the aluminum layer deposited onto the filming layer 30 also is less smooth in the corners of the screen and a greater number of openings, such as cracks, pores, or other discontinuities, 32 exist in the corners than elsewhere in the aluminum layer 23. Thus, a higher percentage of light emitted from the phosphors in the corners of the screen pass through the openings 32 in the aluminum layer rather than are reflected outwardly through the viewing faceplate 18. This light loss creates non-uniform or dark corners which may, if severe enough, cause rejection of the finished CRT screen. A setup for performing a non-destructive test to measure the quality of the screen, more specifically the quality of the filming layer 30 and the overlying aluminum layer 23, before the screen is baked out is shown in FIGS. 2 and 3. A radiation source 40, such as an ultraviolet light having a peak emission at a wavelength of 365 nanometer, is positioned at a distance of about 1 meter from the aluminum layer 23 on the faceplate panel 12. UV radiation from the source 40 is incident on the aluminum layer 23. A detector, such as a CCD camera 42 also is positioned about 1 meter from the aluminum layer 23. UV radiation incident on the aluminum layer 23 passes through the openings 32 in the aluminum layer and stimulates the phosphors of the screen 22 to emission. The light emitted by the phosphors of the screen 22 is propagated in directions defined by a Lambertian-type function. Some of the light is directed inwardly and passes through the filming layer 30 where it is reflected by the aluminum layer 23 and directed outwardly through the viewing faceplate 18. However, a small percentage of this light passes through the openings 32 in the aluminum layer 23 and is focused on the CCD camera 42 by a lens 44. The CCD camera 42 has three channels, a blue, a green and a red channel, each of which contains a 480×512 pixel CCD. As is known in the art, the CCD camera 42 uses a prism to split in incoming light into blue, green and red components from the blue-, green- and red-emitting phosphors of the screen 22. A UV filter 43 is disposed between the UV radiation source 40 and the CCD camera 42 to block any UV radiation from entering the CCD camera. The UV filter 43 may be any non-UV transmitting glass or plastic, such as LEXAN™, available from General Electric Co., Pittsfield, Mass. Because the intensity of the light from the green- and red- emitting phosphors is greater than that of the blue-emitting phosphors, the green and red light incident on the CCD's in the green and red channels, respectively, of the CCD camera 42 provide stronger signals than does the blue light. Accordingly, either the green or red output of the CCD may be utilized to determine the amount of light emitted through the aluminum and picked up by the CCD camera 42. If the aluminum layer 23 had no openings 32, then no light would pass therethrough and the phosphors of the screen 22 would not be stimulated to emission by the UV radiation. Thus, no visible light (blue, green or red) would be measured by the CCD camera. However, as the number of openings 32 in the aluminum layer 23 increases, more visible light is directed back toward the CCD camera 42. A graphical representation of the luminance output of the screen 22 and the quality of the filming layer 30 and of the aluminum layer 23 is evident from the contour map, shown in FIG. 4. The panel 12, used in this test, has a diagonal dimension of 68 cm (hereinafter designated A68). The green light emitted by the screen 22, that is stimulated to emission by the UV source 40, is focused into the CCD camera 42 by lens 44 and is incident on the CCD associated with the green channel of the camera. The output of the green channel CCD is connected to a computer 46 which contains image processing software that groups the luminescence data received from the screen 22 into a data array comprising seventeen data points along the major axis, X, and thirteen data points along the minor axis, Y, of the screen. The luminescence data is communicated to a display device 48, such as a TV screen, a primer, or both. As shown in FIG. 4, the luminescence from the green-emitting phosphors is substantially uniform, 1.0%, or less, across the screen 22, except in the corners where the luminescence increases to values within the range of 3.0 to 6.0%. This is considered an acceptable level of luminescence through the aluminum layer 23 and means that in the corners, 94 to 97% of the light emitted from the green-emitting phosphor elements is emitted or reflected outwardly through the viewing faceplate 18, with only about 3 to 6% being lost through the openings 32 in the aluminum layer. Elsewhere on the screen, between 99 to 100% of the light from the green-emitting phosphors is emitted or reflected outwardly through the viewing faceplate 18. If this test had indicated that excessive light was being lost at the corners of the luminescent screen 22, the filming process would have been investigated to ensure that adequate filming material was present in the corners of the screen. If the filming process was determined to be adequate, then the screen could be aluminized a second time to reduce the light loss by reducing the number or size of the openings 32 in the aluminum layer 23, thereby salvaging the luminescent screen. This is preferable to sealing the faceplate panel to the funnel to complete the manufacturing of the CRT, and then finding that the tube must be rejected for excessive light loss, i.e., dark corners on the screen.

Figure 5:
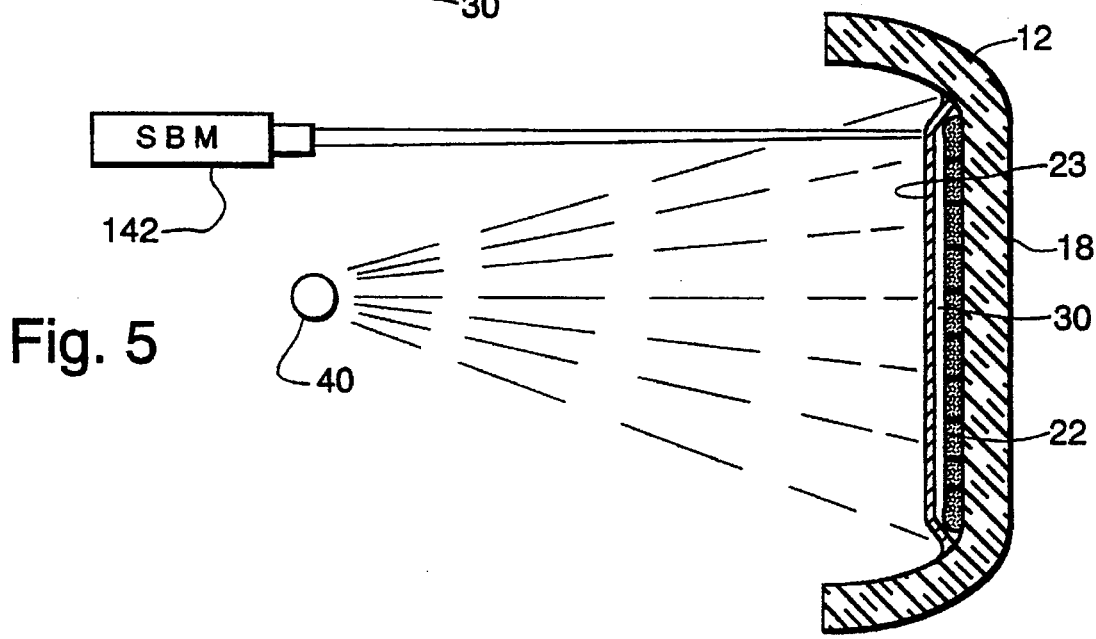
FIG. 5 is a schematic representation of an alternative test setup according to the present invention.

An alternative to using the CCD camera 42 as a detector is shown in FIG. 5. In this second test embodiment, the detector is a photometer, or spot brightness meter, 142 which samples small object areas of the screen, usually at the center of the screen and in the corners. Typically, the sampled areas are 0.5 cm×1.0 cm. The UV source 40 is used to irradiate the aluminum layer 23 of the screen 22. As described above, UV radiation enters the aluminum layer 23 through openings 32, shown in FIG. 3, and stimulates the underlying phosphor screen 22. The spot brightness meter 142 is focused onto one of the sample areas and the luminance therefrom is measured. TABLE 1 summarizes the results of a test conducted on seventy nine A 68 faceplate panels. The panels initially were measured after filming but before being sealed to funnels to make CRT's. These panels are designated "Black Light Panels". Measurements were made in the center and in the 2 o'clock corner using the test setup shown in FIG. 5. After the panels were processed into CRT's, the finished tubes were measured again for light output, but from the front surface, i.e., through the viewing faceplate 18. This front surface test is conventional and is not shown. Measurements through the viewing faceplate also were made in the center of the screen and in the corner. The conclusion, that the light output measured in the center of the viewing faceplate for the finished CRT's was negligible, is based on a comparison of the measured values of the light output from the screen 22, using the present test, with the theoretical values derived by assuming a typical phosphor efficiency of 29 lumens/Watt. This comparison leads to the assignment of a negligibly low (~2%) value for the aluminum transmittance to UV radiation and to visible light, at the center of the screen.

TABLE 1

| SAMPLE DESIGNATION | CENTER | CORNER |
| --- | --- | --- |
| Black Light, Panels | 2% Aluminum Transmittance in Center | 15% Aluminum Transmittance in Corner |
| Light Output, Tubes | Negligible Light Output Loss Due to Filming/Aluminizing Deficiencies | 15% Light Output Loss Due to Filming/Aluminizing Deficiencies |

A drawback of using the spot brightness meter to make the luminescence measurements, according to the method of FIG. 5, is that a plurality of individual measurements must be made in different areas of the screen. Whereas, using a CCD, the entire screen can be simultaneously imaged and a contour map of the luminescence can be created to show not only a comparison of center-to-corner light output, but also the luminescence uniformity of the entire screen.

What is claimed is:

1. A method of determining the quality of an aluminized, luminescent screen for a CRT comprising a luminescent screen having a plurality of color-emitting phosphors disposed on an interior surface of a faceplate panel with an aluminum layer overlying said luminescent screen, said method including the steps of:

uniformly exposing said aluminum layer to ultraviolet radiation; and measuring the luminescence emitted by at least one of said plurality of color-emitting phosphors through said aluminum layer.

2. The method as described in claim 1, wherein said aluminized, luminescent screen further includes a filming layer disposed between said luminescent screen and said aluminum layer.

3. A method of determining the quality of an aluminized, luminescent screen for a CRT comprising a luminescent screen consisting of a plurality of blue-, green- and red-emitting phosphor triads formed on an interior surface of a faceplate panel with an aluminum layer disposed on said luminescent screen, said method including the steps of:

uniformly exposing said aluminum layer to ultraviolet radiation;

measuring the luminescence emitted by at least one of said plurality of color-emitting phosphors through said aluminum layer across said luminescent screen; and visually presenting the luminance emitted as a function of location on said luminescent screen.

4. The method as described in claim 3, wherein said aluminized, luminescent screen further includes a filming layer disposed between said luminescent screen and said aluminum layer.

5. A method of determining the quality of an aluminized, luminescent screen for a CRT comprising a plurality of blue-, green- and red-emitting phosphor triads formed on an interior surface of a substantially rectangular faceplate panel, a filming layer overlying said luminescent screen with an aluminum layer disposed on said filming layer, said method including the steps of:

uniformly exposing said aluminum layer to ultraviolet radiation for a source;

imaging the luminescence emitted by at least one of said plurality of color-emitting phosphors through said aluminum layer across said screen onto a detector;

processing the imaged luminance from said screen to provide a luminance data array; and visually presenting the luminance data array as a function of location on said luminescent screen.

\* \* \* \* \*